(12) United States Patent
Moser et al.

(10) Patent No.: US 7,198,621 B2
(45) Date of Patent: Apr. 3, 2007

(54) ATTACHMENT ASSEMBLY FOR ABSORBENT ARTICLE

(75) Inventors: Julie A. Moser, Cold Spring, KY (US); Alan F. Schleinz, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 537 days.

(21) Appl. No.: 10/326,776

(22) Filed: Dec. 19, 2002

(65) Prior Publication Data

US 2004/0122406 A1    Jun. 24, 2004

(51) Int. Cl.
*A61F 13/20* (2006.01)

(52) U.S. Cl. .................. 604/385.22; 604/391

(58) Field of Classification Search ........... 604/385.22, 604/391, 385.01–385.21, 385.23–385.31
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,618,608 A | 11/1971 | Brink | |
| 3,692,618 A | 9/1972 | Dorschner et al. | |
| 3,802,817 A | 4/1974 | Matsuki et al. | |
| 3,849,241 A | 11/1974 | Butin et al. | |
| 4,340,563 A | 7/1982 | Appel et al. | |
| 4,374,888 A | 2/1983 | Bornslaeger | |
| 4,425,128 A | 1/1984 | Motomura | |
| 4,443,513 A | 4/1984 | Meitner et al. | |
| 4,615,695 A | 10/1986 | Cooper | |
| 4,663,220 A | 5/1987 | Wisneski et al. | |
| 4,704,116 A | 11/1987 | Enloe | |
| 4,781,962 A | 11/1988 | Zamarripa et al. | |
| 4,798,603 A | 1/1989 | Meyer et al. | |
| 4,965,122 A | 10/1990 | Morman | |
| 4,981,747 A | 1/1991 | Morman | |
| 5,057,368 A | 10/1991 | Largman et al. | |
| 5,069,970 A | 12/1991 | Largman et al. | |
| 5,087,253 A | 2/1992 | Cooper | |
| 5,108,385 A | 4/1992 | Snyder | |
| 5,112,326 A | 5/1992 | Quadrini | |
| 5,114,781 A | 5/1992 | Morman | |
| 5,176,668 A | 1/1993 | Bernardin | |
| 5,176,671 A | 1/1993 | Roessler et al. | |
| 5,192,606 A | 3/1993 | Proxmire et al. | |

(Continued)

FOREIGN PATENT DOCUMENTS

EP    217 032    4/1987

(Continued)

*Primary Examiner*—Tatyana Zalukaeva
*Assistant Examiner*—Ginger Chapman
(74) *Attorney, Agent, or Firm*—Pauley Peterson & Erickson

(57) ABSTRACT

A disposable diaper having an attachment assembly including a subassembly bonded or attached to an exterior surface of a front waist region of the diaper and extending laterally from opposing side edges of the front waist region to form laterally opposing front ears. A reduced-size attachment panel is properly positioned and bonded to the subassembly to improve the functionality of a fastening system of the diaper without interfering with or limiting the extensibility of the diaper chassis, while minimizing the use of relatively expensive attachment panel material.

19 Claims, 7 Drawing Sheets

U.S. PATENT DOCUMENTS

| | | |
|---|---|---|
| 5,226,992 A | 7/1993 | Morman |
| 5,236,430 A | 8/1993 | Bridges |
| 5,244,482 A | 9/1993 | Hassenboehler, Jr. et al. |
| 5,246,433 A | 9/1993 | Hasse et al. |
| 5,277,976 A | 1/1994 | Hogle et al. |
| 5,374,262 A | 12/1994 | Keuhn, Jr. et al. |
| 5,403,302 A | 4/1995 | Roessler et al. |
| 5,445,628 A | 8/1995 | Gipson et al. |
| 5,466,410 A | 11/1995 | Hills |
| 5,509,915 A | 4/1996 | Hanson et al. |
| 5,611,789 A | 3/1997 | Seth |
| 5,624,420 A | 4/1997 | Bridges et al. |
| 5,624,428 A * | 4/1997 | Sauer .................. 604/391 |
| 5,660,666 A | 8/1997 | Dilnik et al. |
| 5,695,868 A | 12/1997 | McCormack |
| 5,795,350 A | 8/1998 | Schmitz |
| 5,843,056 A | 12/1998 | Good et al. |
| 5,851,205 A * | 12/1998 | Hisada et al. ............ 604/390 |
| 5,897,545 A * | 4/1999 | Kline et al. ............. 604/386 |
| 5,931,823 A | 8/1999 | Stokes et al. |
| 6,022,430 A * | 2/2000 | Blenke et al. ........... 156/73.1 |
| 6,099,516 A | 8/2000 | Pozniak et al. |
| 6,306,121 B1 | 10/2001 | Damaghi et al. |
| 6,363,587 B1 | 4/2002 | Richter et al. |

FOREIGN PATENT DOCUMENTS

| | | |
|---|---|---|
| EP | 717 273 | 6/1996 |
| WO | 83/01338 | 4/1983 |
| WO | WO 01/43682 A1 * | 6/2001 |
| WO | WO 01/70155 A1 * | 9/2001 |

* cited by examiner

ATTACHMENT ASSEMBLY FOR ABSORBENT ARTICLE

FIELD OF INVENTION

The present invention relates to disposable absorbent articles. More particularly, the present invention relates to an attachment assembly for a fastening system of the absorbent article that does not interfere with the extensibility of the article materials and/or article components.

BACKGROUND OF THE INVENTION

Absorbent articles such as diapers, training pants or incontinence garments typically include a liner material, an absorbent core and a liquid impervious back sheet, or outer cover. Such articles desirably provide a close, comfortable fit about the wearer and contain body exudates. Conventional diapers, for example, may include elastic or extensible materials and/or components that desirably stretch or extend to allow the diaper to fit properly about the waist area and hips of the wearer, for example. However, many conventional diapers further include fastening systems that interfere or limit the extensibility of the diaper.

For example, conventional diapers may include an attachment area including a loop-type fastening component or material that extends laterally across a front portion of the diaper. The relatively higher cost loop material is typically made of an inelastic or non-extensible material, such as a pattern unbonded material and interferes with or limits the extensibility of the diaper materials, for example an extensible outer cover. Additionally, the fastening component may be bonded directly or indirectly to a back waist region of the diaper. For example, the fastening component may be bonded to the back waist region or to a fastener that extends from a side edge of the back waist region using conventional bonding means and bonding patterns, such as a zig-zag bond pattern. The bond line or area where the loop material is bonded to the back portion of the diaper limits the extensibility of the other diaper components, such as a stretchable or extensible fastening component. As a result, the diaper chassis does not stretch or extend to properly conform to or cover the wearer's body. For example, the conventional chassis may not stretch or extend to cover the wearer's buttocks and hips and/or provide a seal about the wearer's legs. Thus, the conventional diapers do not provide adequate coverage and/or seal, which can undesirably result in improper fit and/or leakage. As a result, many of these articles have not contained bodily exudates as effectively as desired.

Accordingly, despite the attempts to develop improved diapers and other absorbent articles, there remains a need for a diaper having a fastening system that does not interfere with the extensibility of the diaper chassis and, thus, provides for proper positioning of the diaper about the waist of the wearer and effective containment of bodily exudates.

SUMMARY OF THE INVENTION

In response to the difficulties and problems discussed above, the present invention provides a diaper having an attachment assembly including a subassembly that extends laterally from opposing side edges of a front waist region of the diaper to provide laterally opposing front chassis ears, without interfering with the extensibility of the chassis, and a reduced-size attachment panel that is optimally positioned on the subassembly in order to eliminate errant attachment of a fastening system to the attachment panel, while minimizing manufacturing and material costs.

The diaper of the present invention defines a front waist region, a back waist region, and a crotch region that extends between and connects the front waist region and the back waist region. The front waist region includes the portion of the absorbent article that, when worn, is positioned on the front of the wearer while the back waist region includes the portion of the absorbent article that, when worn, is positioned on the back of the wearer. The crotch region includes the portion of the absorbent article that, when worn, is positioned between the legs of the wearer and covers the lower torso of the wearer.

The diaper of the present invention includes an extensible outer cover and an extensible bodyside liner that is connected to the outer cover in a superposed relation. An absorbent core is located between the outer cover and the bodyside liner to define a chassis of the diaper that forms the waist opening and each leg opening. The absorbent core is configured to contain and/or absorb body exudates discharged from the wearer.

In one embodiment of this invention, the attachment assembly is applied or bonded to the outer surface of the extensible outer cover at the front waist region. The attachment assembly includes a subassembly applied to the front waist region, and extending laterally from the side edges of the front waist region to form laterally opposing front ears. The subassembly may be applied to the outer cover using any suitable bonding or attachment means known to those skilled in the art, provided the bonding or attachment means does not limit the lateral extensibility of the diaper components bonded or attached to the subassembly.

The subassembly desirably is made of a low-cost, soft, breathable material that provides converting machine processability, softness and fit attributes that current absorbent articles cannot provide. Suitable materials include, but are not limited to, nonwoven meltblown, spunbond or bonded-carded webs, knit or woven materials and laminates of suitable materials.

In one embodiment of this invention, the subassembly includes a first layer of material applied to the outer cover. A material strip is positioned at each end portion of the first layer of material corresponding to a front ear of the subassembly. Desirably, the material strip runs longitudinally along each end portion to provide stiffness and strength to the subassembly. The material strips can be attached or bonded to the end portions using suitable bonding means known to those skilled in the art, such as ultrasonic bonding or adhesive bonding for example. Suitable materials for the material strips include, but are not limited to, nonwoven materials and laminates thereof. For example, in one embodiment of this invention, the material strips may be a spunbond material, a polypropylene material, or a spunbond-meltblown-spunbond (SMS) laminate material.

In one embodiment of this invention, a second layer of material can be positioned with respect to the first layer and applied thereto so that at least a portion of the material strips are covered by the second layer. Desirably, the second layer has similar dimensions to first layer and is positioned with respect to the first layer in a superposed relation with the material strips sandwiched or positioned between the first layer and the second layer.

A reduced-size attachment panel is attached to the subassembly. The attachment panel may be applied to the subassembly during an off-line process or the attachment panel may be cut and placed onto the subassembly before or after the subassembly is applied to the front waist region.

Desirably, the attachment panel is made of a pattern unbonded ("PUB") material having loop engagement means for mechanically engaging at least one fastener connected with respect to the back waist region. The attachment panel is positioned on the subassembly and has suitable dimensions for proper alignment of the fasteners on the attachment panel to provide the intended hook-to-loop engagement of the fasteners to the attachment panel. The limited dimensions of the attachment panel ensure proper placement of the fasteners on the attachment panel, while minimizing the amount of relatively expensive material used to make the attachment panel.

The multiple component attachment assembly allows the function of the front waist region ears to be decoupled from the function of the attachment assembly. This decoupling minimizes the use of expensive PUB material, for example, while improving the incidence of the proper engagement of the hook-to-loop fastening system of the absorbent article.

BRIEF DESCRIPTION OF THE DRAWINGS

These and other objects and features of this invention will be better understood from the following detailed description taken in conjunction with the drawings, wherein.

DESCRIPTION OF PREFERRED EMBODIMENTS

Definitions

Figure 1:
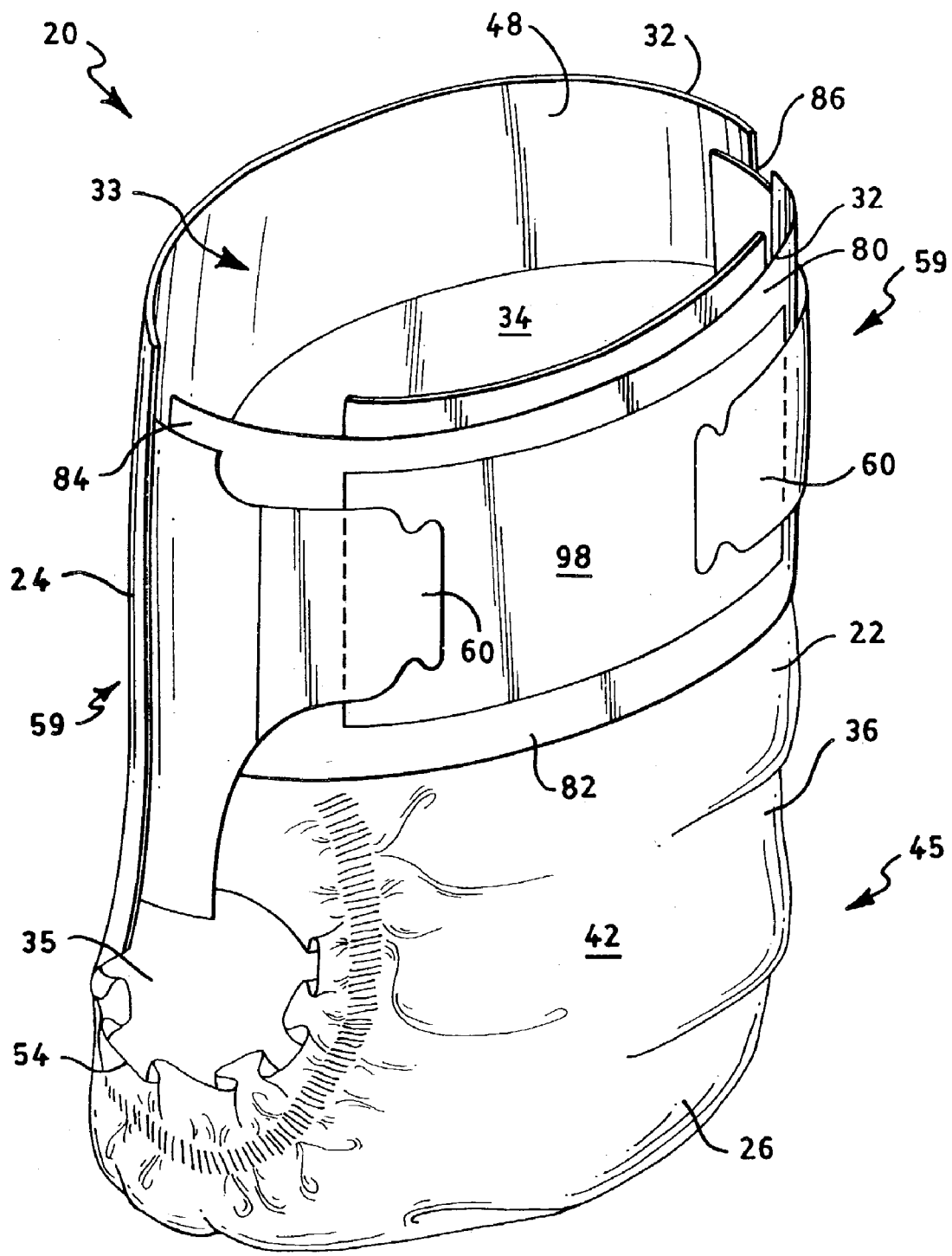
FIG. 1 representatively shows a perspective view of a disposable diaper, according to one embodiment of this invention.
Figure 2:
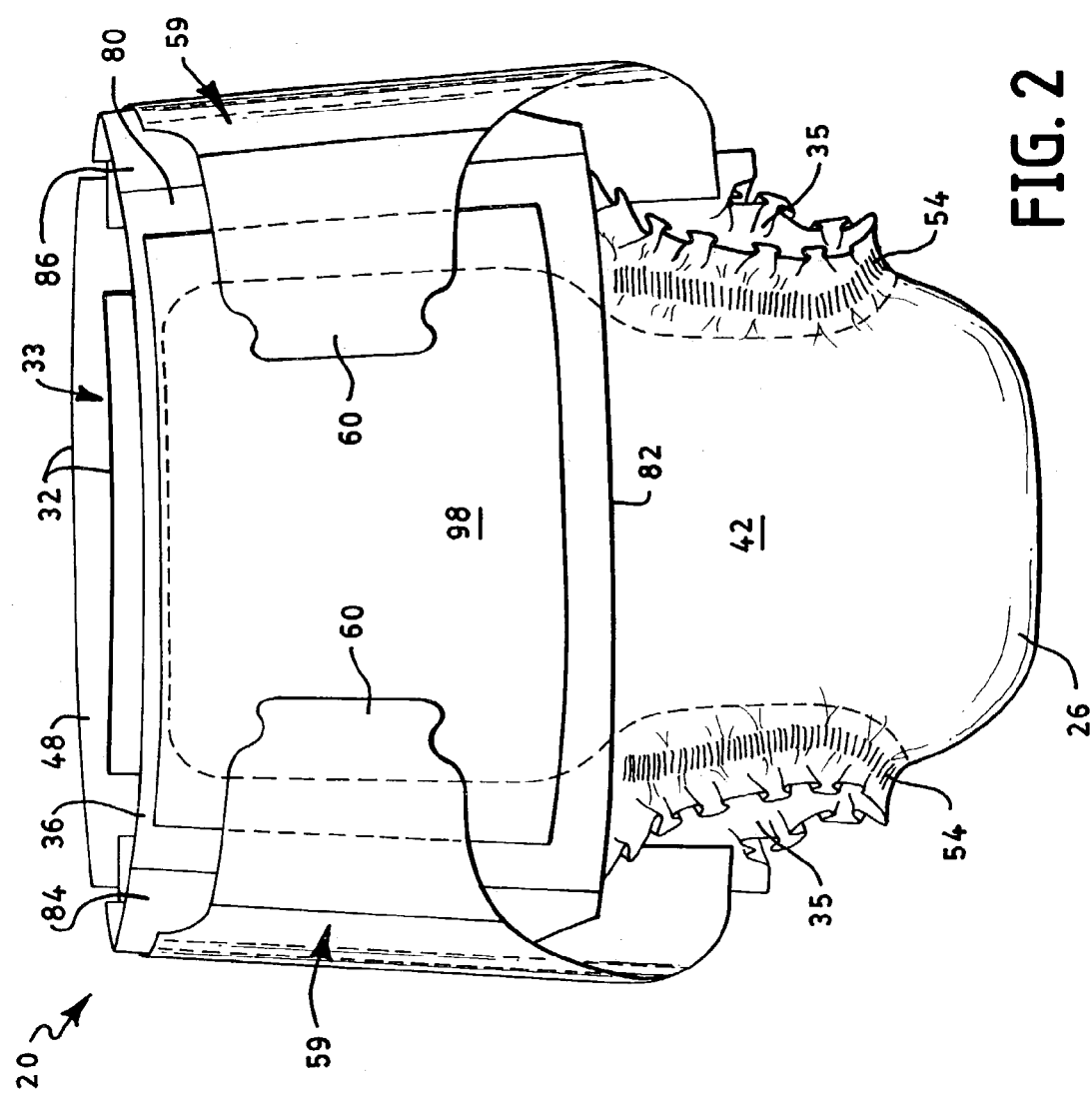
FIG. 2 representatively shows a front elevation view of the disposable diaper of FIG. 1, according to one embodiment of this invention.

As used herein, the term "bonded-carded web" refers to webs that are made from staple fibers which are sent through a combing or carding unit, which separates or breaks apart and aligns the staple fibers in the machine direction to form a generally machine direction-oriented fibrous nonwoven web. Such fibers are usually purchased in bales, which are placed in an opener/blender or picker, which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

As used herein, the term "disposable" includes being disposed of after usually a single use and not intended to be washed and reused.

As used herein, the terms "elastic," "elasticized" and "elasticity" refer to a property of a material or composite by virtue of which the material or composite tends to recover its original size and shape after removal of a force causing a deformation.

As used herein, the term "elastomeric" refers to a material or composite which can be elongated by at least 50 percent of its relaxed length in any direction and which will recover, upon release of the applied force, at least 40 percent of its elongation. It is generally desired that the elastomeric material or composite be capable of being elongated by at least 100 percent, more desirably by at least 300 percent, of its relaxed length and recover, upon release of an applied force, at least 50 percent of its elongation.

As used herein, the term "extensible" refers to a material or composite which can be elongated by at least 50% of its relaxed length in any direction and tends not to recover, or recovers less than 40% of its elongation, after removal of a force causing a deformation.

As used herein, the term "inelastic" refers to materials, which are not elastomeric, either because they cannot be sufficiently stretched by the above amount or because they do not sufficiently retract by the above amount when stretched and relaxed.

As used herein, the term "layer" when used in the singular can have the dual meaning of a single element or a plurality of elements.

As used herein, the terms "longitudinal" and "transverse" have their customary meanings. The longitudinal axis lies in the plane of the article when laid flat and fully extended and is generally parallel to a vertical plane that bisects a standing wearer into left and right body halves when the article is worn. The transverse axis lies in the plane of the article generally perpendicular to the longitudinal axis.

As used herein, the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241. Meltblown fibers are microfibers, which may be continuous or discontinuous, are generally smaller than 10 microns in average diameter, and are generally tacky when deposited onto a collecting surface.

As used herein, the terms "necked" and "neck stretched" are interchangeable terms that refer to a method of elongating an inelastic nonwoven fabric, generally in the longitudinal, or machine direction of the fabric, to reduce its width in a controlled manner to a desired amount. The controlled stretching may take place under cool, room temperature, or greater temperatures, and is limited to an increase in overall dimension in the direction being stretched up to the elongation required to break the fabric, which in most cases is about 1.2 to 1.4 times an original length. The resulting neck-stretched fabric can be extended in the lateral (cross-machine) direction of the fabric during subsequent use, causing the fabric to return toward its original pre-necked configuration. Neck stretching processes are disclosed, for example, in U.S. Pat. No. 4,443,513 to Meitner et al.; U.S. Pat. No. 4,965,122, U.S. Pat. No. 4,981,747 and U.S. Pat. No. 5,114,781 to Morman; and U.S. Pat. No. 5,244,482 to Hassenboehler Jr. et al.

As used herein, the term "passive bond" refers to a bond that has a relatively low peel strength such that the bond can be easily broken by hand if desired to assist in inspecting or removing an absorbent article from the wearer, without tearing or severely damaging the other portions of the article, and without causing trauma to the wearer or spillage of waste material from the absorbent article.

As used herein, the term "pattern unbonded" or interchangeably "point unbonded" or "PUB," means a fabric pattern having continuous bonded areas defining a plurality of discrete unbonded areas. The fibers or filaments within the discrete unbonded areas are dimensionally stabilized by the continuous bonded areas that encircle or surround each unbonded area, such that no support or backing layer of film or adhesive is required. The unbonded areas are specifically designed to afford spaces between fibers or filaments within the unbonded areas. A suitable process for forming the pattern-unbonded nonwoven material of this invention includes providing a nonwoven fabric or web, providing oppositely positioned first and second calender rolls and defining a nip therebetween, with at least one of said rolls being heated and having a bonding pattern on its outermost surface comprising a continuous pattern of land areas defining a plurality of discrete openings, apertures or holes, and passing the nonwoven fabric or web within the nip formed by said rolls. Each of the openings in said roll or rolls defined by the continuous land areas forms a discrete unbonded area in at least one surface of the nonwoven fabric or web in which the fibers or filaments of the web are substantially or completely unbonded. Stated alternatively, the continuous pattern of land areas in said roll or rolls forms a continuous pattern of bonded areas that define a plurality of discrete unbonded areas on at least one surface of said nonwoven fabric or web. Alternative embodiments of the aforesaid process include pre-bonding the nonwoven fabric or web before passing the fabric or web within the nip formed by the calender rolls, or providing multiple nonwoven webs to form a pattern-unbonded laminate. PUB fabrics are disclosed in U.S. patent application Ser. No. 08/754,419, commonly assigned, the disclosure of which is incorporated herein by reference.

Alternative applications in which PUB fabric may be used include those having film applied during the formation of the PUB fabric where the film will provide a liquid barrier so that it may be used as a clothlike outer cover for a personal care product.

As used herein, the term "permanently bonded" refers to the joining, adhering, connecting, attaching, or the like, of two elements of an absorbent article such that the elements tend to be and remain bonded during normal use conditions of the absorbent article.

As used herein, the term "prefastened" refers to a condition wherein the absorbent article has a fastening feature, which is engaged or fastened prior to use by the wearer. For example, the fastening feature of the absorbent article may be engaged or fastened during the manufacturing process.

As used herein, the term "refastenable" refers to the property of two elements being capable of releasable attachment, separation, and subsequent releasable reattachment without substantial permanent deformation or other damage to either element.

As used herein, the term "releasably attached," "releasably engaged," and variations thereof refer to two elements being connected or connectable such that the elements tend to remain connected absent a separation force applied to one or both of the elements and the elements being capable of separation without substantial permanent deformation or other damage. The required separation force is typically beyond that encountered while wearing the absorbent article.

As used herein, the term "spunbond fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein, "ultrasonic bonding" means a process performed, for example, by passing the fabric between a sonic horn and anvil roll as illustrated in U.S. Pat. No. 4,374,888 to Bornslaeger.

The various aspects and embodiments of the present invention will be described in the context of disposable absorbent articles, and more particularly referred to, without limitation and by way of illustration only, as a disposable diaper. It is apparent that the articles and methods of the present invention are equally adaptable for other types of absorbent articles, such as training pants, adult incontinence articles, feminine care articles, other personal care garments, medical or health care garments, and other disposable articles and garments.

The diaper 20 of the present invention includes an attachment assembly 80 comprising a subassembly 82 attached or bonded to a front waist region 22 of the diaper 20 and an attachment panel 98 attached or bonded to the subassembly 82. The subassembly 82 extends laterally from opposing side edges of the front waist region 22 to form a first front ear 84 and a laterally opposing second front ear 86. The subassembly 82 is attached or bonded to the front waist region 22 without interfering with the extensibility of the extensible chassis materials in at least the cross-machine or lateral direction. The opposing front ears 84, 86 provide hip coverage and assist the caregiver in positioning the diaper 20 on the child and provide the caregiver the sense that the diaper is "swaddling" the child. Additionally, in one embodiment of this invention, the ears 84, 86 each include a longitudinally positioned SMS laminate material strip that provides stiffness to the front ears 84, 86. The added stiffness prevents movement, such as rotating or shifting of the front waist region 22 with respect to the back waist region 24, and maintains an ideal fit about the wearer's waist to prevent leakage at the leg openings, for example. Desirably, the attachment panel 98 has reduced dimensions, relative to the subassembly 82, and is optimally positioned with respect to the front ears in order to eliminate errant attachment of a fastening system 59 with the attachment panel 98, while minimizing manufacturing costs.

Figure 3:
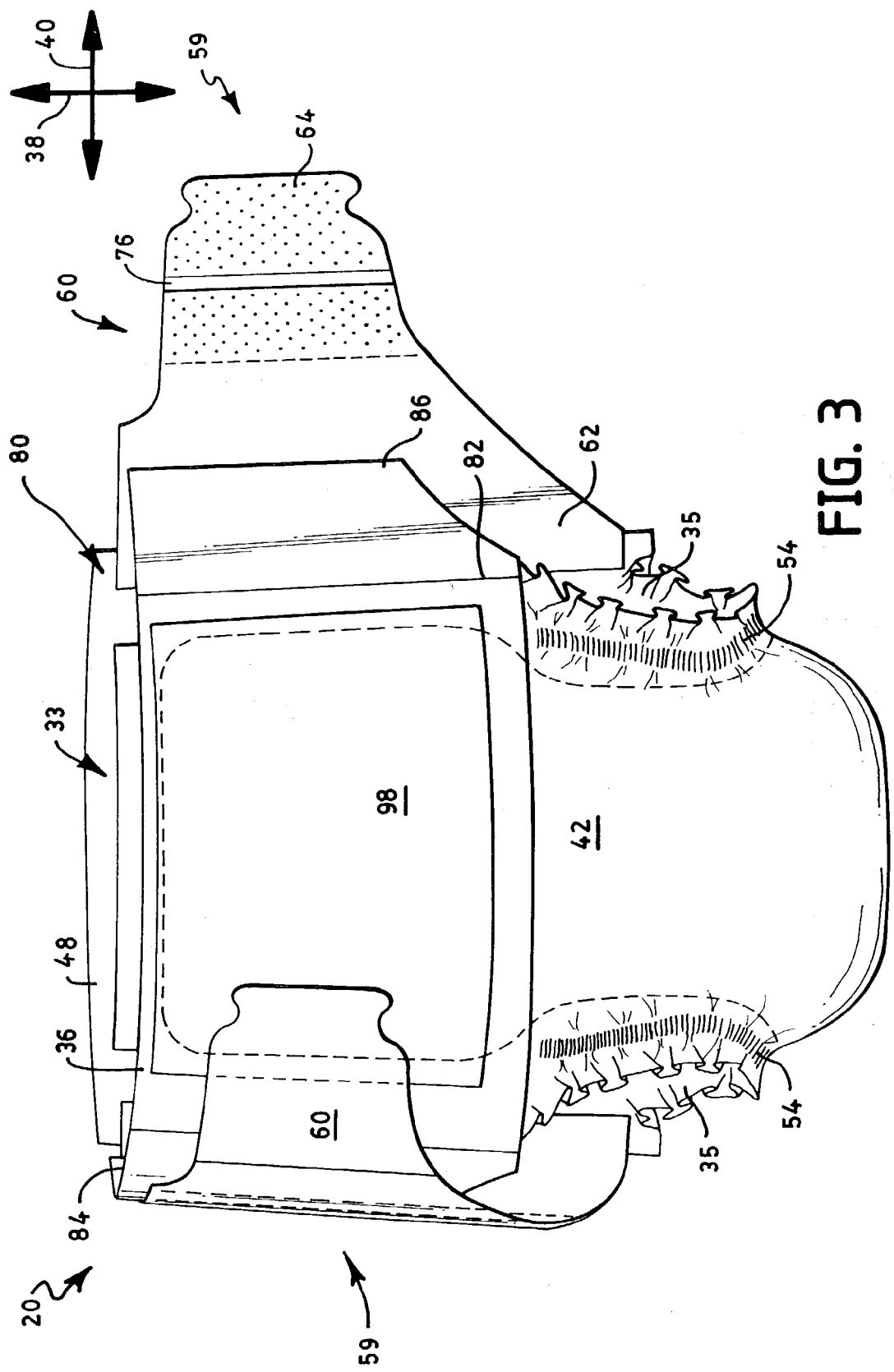
FIG. 3 representatively shows a front elevation view of the disposable diaper of FIG. 1 with a waist size adjustment means in an unengaged position, according to one embodiment of this invention.
Figure 4:
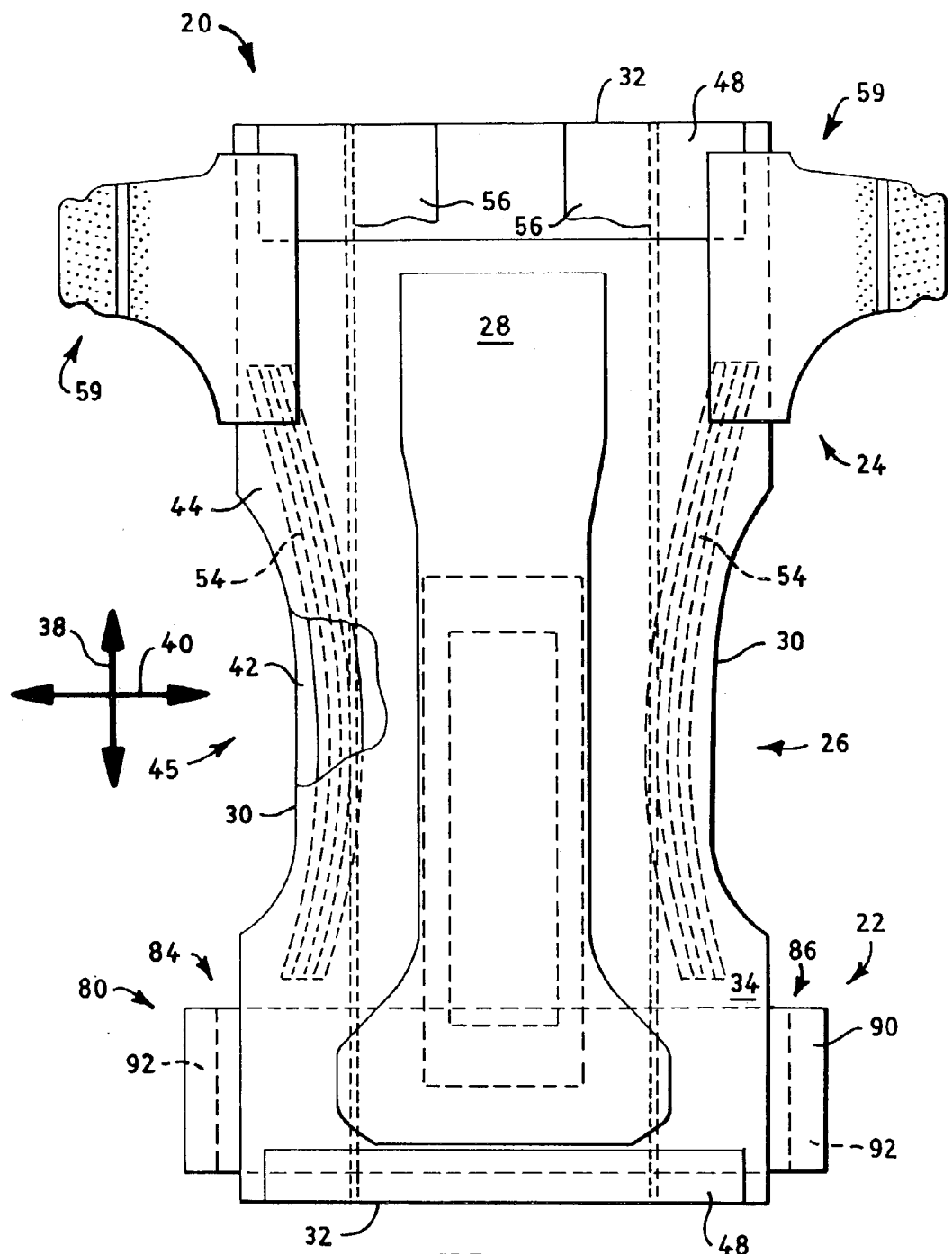
FIG. 4 representatively shows a plan view of the disposable diaper of FIG. 1 in an unfastened, stretched and laid flat condition with a surface of the diaper that contacts the wearer's skin facing the viewer, according to one embodiment of this invention.
Figure 5:
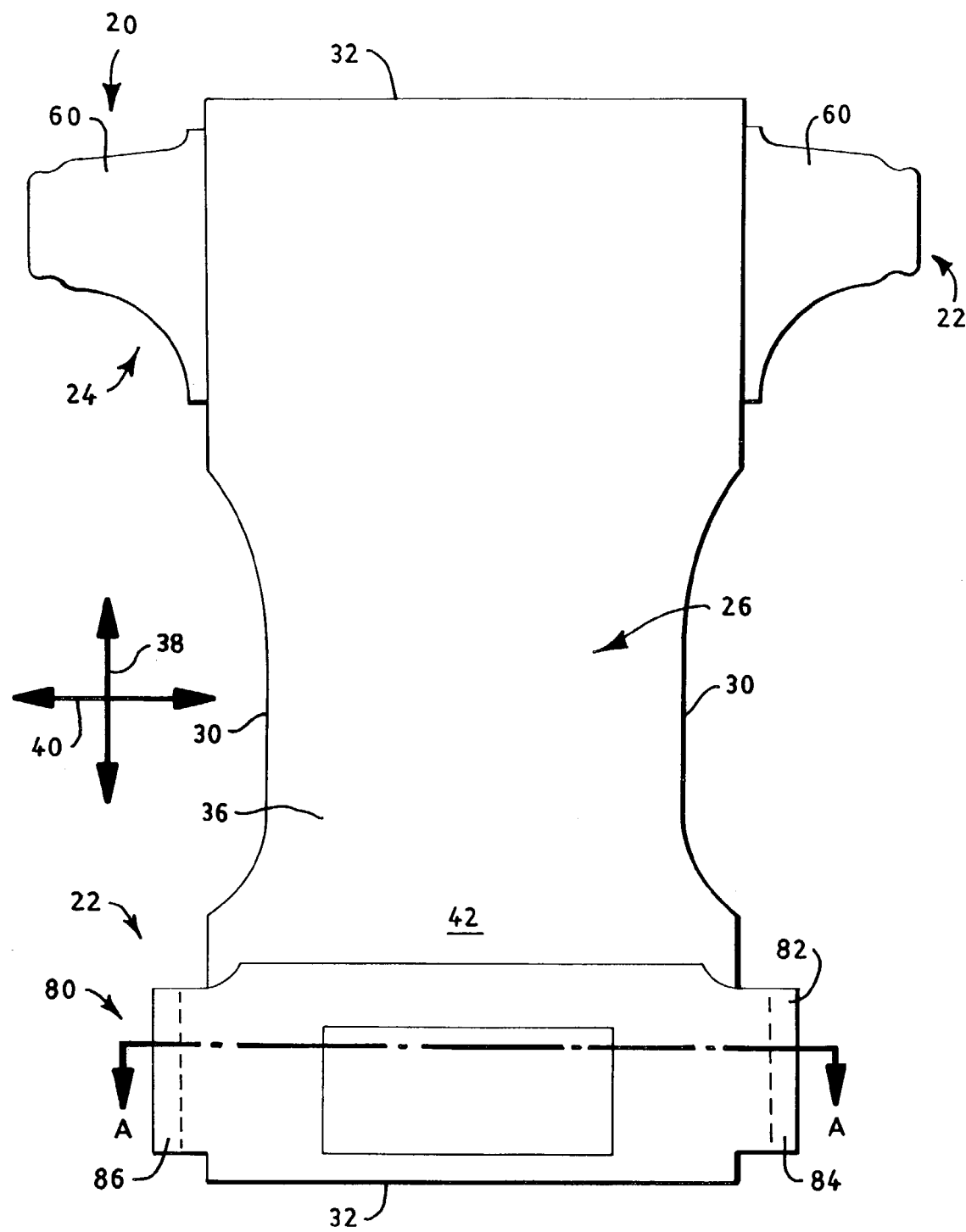
FIG. 5 representatively shows a plan view of the disposable diaper of FIG. 1 in an unfastened, stretched and laid flat condition with a surface of the diaper that contacts the wearer's skin facing away from the viewer, according to one embodiment of this invention.

Referring to FIGS. 1–5, a disposable diaper 20 of the present invention defines a front waist region 22, a back waist region 24, and an intermediate or crotch region 26 that extends between and connects the front waist region 22 and the back waist region 24. For reference, arrows 38 and 40 depicting the orientation of the longitudinal axis and the transverse or lateral axis, respectively, of the diaper 20 are illustrated in FIGS. 3–5.

The front waist region 22 includes the portion of the diaper 20 that, when worn, is positioned on the front of the wearer while the back waist region 24 includes the portion of the diaper 20 that, when worn, is positioned on the back of the wearer. The crotch region 26 of the diaper 20 includes the portion of the diaper 20 that, when worn, is positioned between the legs of the wearer and covers the lower torso of the wearer.

The diaper 20 defines a pair of laterally opposing side edges 30, a pair of longitudinally opposing waist edges 32, an interior surface 34 that is configured to contact the wearer, and an exterior surface 36 opposite the interior surface 34 that is configured to contact the wearer's clothing during use. As shown in FIGS. 1–5, the diaper 20 also includes an outer cover 42 and a bodyside liner 44 that is connected to the outer cover 42 in a superposed relation. An absorbent core 28 is positioned or located between the outer cover 42 and the bodyside liner 44. The outer cover 42, the bodyside liner 44 and the absorbent core 28 define a chassis 45 of the diaper 20, which forms the waist opening 33 and each leg opening 35. The laterally opposing side edges 30 are generally defined by the side edges of the outer cover 42 that further define leg openings 35, which desirably are curvilinear. The waist edges 32 are generally defined by the waist edges of the outer cover 42 and form the waist opening 33 that is configured to encircle the waist of the wearer during use. The absorbent core 28 is configured to contain and/or absorb body exudates discharged from the wearer.

The diaper 20 may be of various suitable shapes. For example, in the unfastened configuration as shown in FIGS. 4 and 5, the diaper 20 may have an overall rectangular shape, T-shape or an approximate hourglass shape. In the shown embodiment, the diaper 20 has a generally I-shape in an unfastened configuration. Examples of diaper configurations suitable for use in connection with the instant application and other diaper components suitable for use on diapers are described in U.S. Pat. No. 4,798,603 issued Jan. 17, 1989 to Meyer et al.; U.S. Pat. No. 5,176,668 issued Jan. 5, 1993 to Bernardin; U.S. Pat. No. 5,192,606 issued Mar. 9, 1993 to Proxmire et al.; and U.S. Pat. No. 5,509,915 issued Apr. 23, 1996 to Hanson et al., the disclosures of which are herein incorporated by reference.

The various components of the diaper 20 are integrally assembled together employing various types of suitable attachment means, such as adhesive, sonic and thermal bonds, and combinations thereof. In the shown embodiment, for example, the outer cover 42 and bodyside liner 44 are assembled to each other and to the absorbent core 28 with an adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, the other components of the diaper 20 may be assembled into the diaper 20 by employing the above-identified attachment mechanisms.

In accordance with one embodiment of this invention, as shown in FIGS. 1–3 and 5, the outer cover 42 is extensible, for example as described in U.S. patent application Ser. No. 09/563,417 filed on May 3, 2000 by Roessler et al. The disclosure of application Ser. No. 09/563,417 is incorporated herein by reference to the extent it assists the present disclosure. The outer cover 42 of the diaper 20 may suitably be composed of a material that is either water vapor permeable or water vapor impermeable. It is generally desired that the outer cover 42 be formed from a material that is substantially impermeable to liquids and permeable (breathable) to water vapor. The outer cover 42 can be manufactured from a thin plastic film or other suitable flexible liquid-impermeable material. For example, the outer cover 42 may be formed from a polyethylene film having a thickness of about 0.013 millimeter (0.5 mil) to about 0.051 millimeter (2.0 mils). If a more clothlike feeling is desired, the outer cover 42 may be formed from a polyolefin film having a nonwoven web, such as a spunbond web of polyolefin fibers, laminated to an exterior surface thereof. For example, a stretch-thinned polypropylene film having a thickness of about 0.015 millimeter (0.6 mil) may have thermally laminated thereto a spunbond web of polypropylene fibers. The polypropylene fibers have a thickness of about 1.5 to 2.5 denier per filament, which nonwoven web has a basis weight of about 17 grams per square meter (0.5 ounce per square yard). The outer cover 42 may otherwise include bicomponent fibers such as polyethylene/polypropylene bicomponent fibers. Methods of forming such clothlike outer covers are known to those skilled in the art.

Further, the outer cover 42 may be formed of a woven or nonwoven fibrous web layer which has been totally or partially constructed or treated to impart a desired level of liquid impermeability to selected regions that are adjacent or proximate the absorbent core 28. Still further, the outer cover 42 may optionally be composed of a microporous "breathable" material, which permits vapors to escape from the absorbent core 28 while still preventing liquid exudates from passing through the outer cover 42. For example, the outer cover 42 may include a vapor permeable nonwoven facing layer laminated to a microporous film. Suitable breathable outer cover materials are described in U.S. Pat. No. 5,695,868, issued to McCormack et al.; and U.S. Pat. No. 5,843,056, issued Dec. 1, 1998 to Good et al., the disclosures of which are incorporated herein by reference. Still further, the outer cover 42 may also be an elastomeric material such as a stretch-thermal laminate (STL), a neck-bonded laminate (NBL), or a stretch-bonded laminate (SBL) material. Methods of making such materials are well known to those skilled in the art and are described in U.S. Pat. No. 4,663,220, issued May 5, 1987 to Wisneski et al.; U.S. Pat. No. 5,226,992, issued Jul. 13, 1993 to Mormon; and European Patent Application No. EP 0 217 032 published on Apr. 8, 1987 in the names of Taylor et al., the disclosures of which are incorporated herein by reference. The outer cover 42 can also be embossed or otherwise provided with a matte finish to provide a more aesthetically pleasing appearance.

In one embodiment of this invention, an attachment assembly 80 is positioned with respect to the front waist region 22. Desirably, the attachment assembly 80 is applied or bonded to the exterior surface 36 of the outer cover 42 using suitable application or bonding means. The attachment assembly 80 comprises a subassembly 82 applied or bonded to the front waist region 22, which extends laterally from the side edges 30 of the front waist region 22 to form a first front ear 84 and a laterally opposing second front ear 86, as shown for example in FIGS. 5 and 6. Any suitable bonding means known to those skilled in the art may be used to attach the subassembly 82 to the exterior surface 36 of the outer cover 42. For example, the subassembly 82 may be ultrasonically bonded, thermally bonded or adhesively bonded to the outer cover 42. Desirably, the subassembly 82 is adhesively bonded to the exterior surface 36 of the diaper 20 using any suitable adhesive, such as an elastic or extensible adhesive material.

In one embodiment of this invention, the front ears 84 and 86 are desirably releasably bonded or attached with respect to the back waist region 24 of the diaper 20. For example, each front ear 84 and 86 may be passively bonded to a corresponding edge portion of the back waist region or a corresponding extensible side panel, which is permanently bonded to the back waist region 24, using suitable ultrasonic bonds and bonding patterns. Such bonding processes are well known in the art.

The subassembly 82 desirably is made of a low-cost, soft, breathable material that provides converting machine processability, softness and fit attributes that current absorbent articles do not provide. Suitable materials include, but are not limited to, nonwoven meltblown, spunbond or bonded-carded webs, knit or woven materials and laminates of suitable materials. In one embodiment of this invention, the subassembly 82 comprises a nonwoven spunbond web. Desirably, but not necessarily, the nonwoven spunbond web has a thickness suitable for graphics printed on the outer cover 42 to be visible through the subassembly 82.

The subassembly 82 may comprise only a first layer of material 88. Alternatively, referring to FIG. 6, in one embodiment of this invention, the subassembly 82 desirably comprises a composite material including the first layer of material 88, for example, a nonwoven spunbond material, attached or bonded to the outer cover 42. The first layer 88 may comprise any suitable material, including but not limited to the materials discussed above with reference to the subassembly 82. A material strip 92 is positioned at each of a first end portion 89 and a second end portion 90 of the first layer of material 88. First end portion 89 and second end portion 90 correspond with first ear 84 and second ear 86 of subassembly 82, respectively. Desirably, but not necessarily, the material strip 92 runs longitudinally along each of the first end portion 89 and the second end portion 90 to provide stiffness and strength to the subassembly 82. The material strips 92 may have any suitable width, for example the materials strips 92 may have a width of about 10 mm to about 40 mm, desirably about 20 mm to about 30 mm. Desirably, the material strips 92 are adhesively bonded to the corresponding end portion 89, 90 using suitable elastic or extensible adhesive materials. Other suitable attachment or bonding means known to those skilled in the art, such as ultrasonic bonding, for example, may also be used to bond or attach the material strips 92 to the first layer of material 88. Suitable materials for the material strips 92 include, but are not limited to, nonwoven materials and laminates thereof. For example, in one embodiment of this invention, the material strips 92 may comprise a spunbond material, a polyethylene and/or polypropylene film material, or a spunbond-meltblown-spunbond (SMS) laminate material. Desirably, the material strips 92 comprise a SMS laminate material that provides the front ears 84, 86 with added stiffness, in order to maintain the diaper ideally positioned about the wearer's waist to prevent shifting or movement of the front waist region 22 with respect to the back waist region 26 and leakage, as discussed above.

Figure 6:
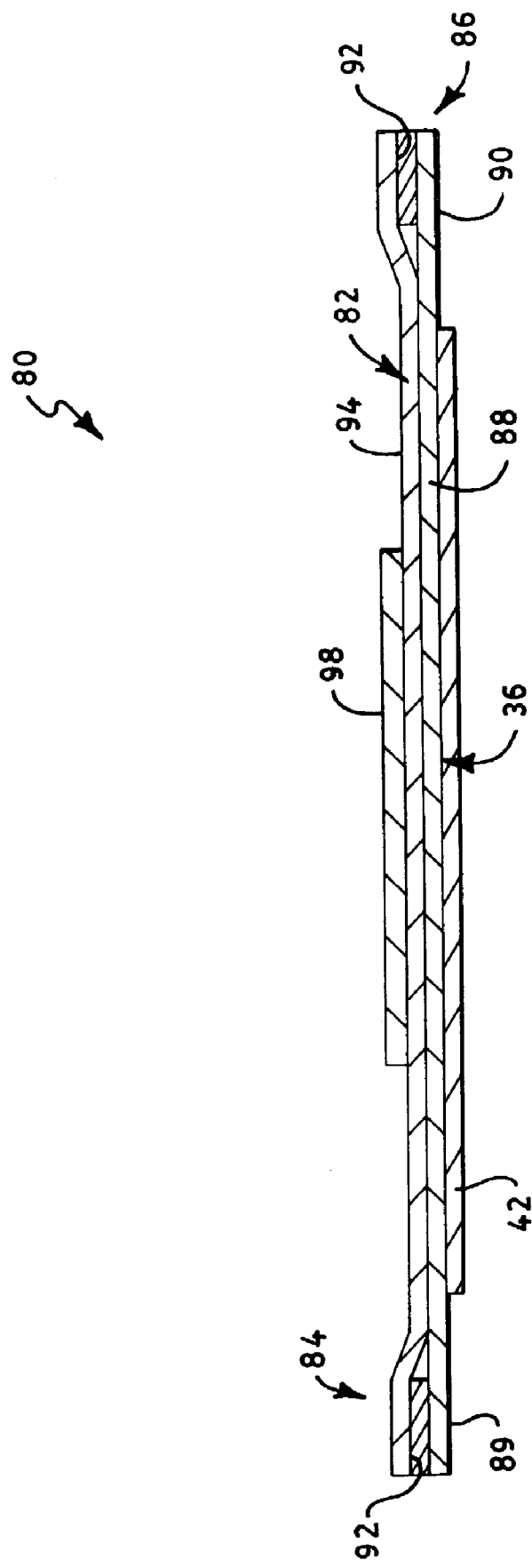
FIG. 6 representatively shows a cross-sectional view, through line A—A as shown in FIG. 5, of an attachment assembly applied to an outer surface of an outer cover, according to one embodiment of this invention.

In one embodiment of this invention, a second layer of material 94 can be positioned with respect to the first layer 88 and bonded or attached thereto such that at least a portion of the first layer 88 and/or at least a portion of each material strip 92 is covered by the second layer 94, as shown in FIG. 6. Desirably, the second layer 94 has similar dimensions to the first layer 88 and is positioned in a superposed relation on the first layer 88 with the material strips 92 sandwiched or positioned between the first layer 88 and the second layer 94. The second layer 94 may comprises any suitable material, as discussed above with reference to the first layer 88. Desirably, but not necessarily, the second layer 94 is made of the same or similar material as the first layer 88, for example a nonwoven spunbond material.

Referring to FIGS. 5 and 6 for example, an attachment panel 98 is bonded or attached to the subassembly 82. For example, the attachment panel 98 may be adhesively bonded to the sub assembly using suitable adhesive materials, such as elastic or extensible adhesive materials. The attachment panel 98 may be applied to the subassembly 82 during an off-line process and subsequently incorporated into the diaper 20, for example at a converting machine, or the attachment panel 98 may be cut and placed onto the subassembly 82 during an in-line process before or after the subassembly 82 is applied to the front waist region 22. The attachment panel 98 may comprise any suitable elastic, extensible or non-extensible material. Desirably, the attachment panel 98 is made of a pattern unbonded (PUB) material, as described above, having loop engagement means for mechanically engaging at least one fastener 60 connected with respect to the back waist region 24, as described below. In one embodiment of this invention, the attachment panel 98 is optimally positioned on the subassembly 82 and has suitable dimensions for proper alignment of the fasteners 60 on the attachment panel 98 to provide the intended hook-to-loop engagement of the fasteners 60 with the attachment panel 98. The limited or reduced dimensions of the attachment panel 98, relative to the subassembly 82 prevent errant hook-loop attachment and ensure proper placement of the fasteners 60 on the attachment panel 98, while minimizing the amount of relatively expensive material used to manufacture the attachment panel 98. The attachment panel 98 may have any suitable shape.

Desirably, the attachment panel 98 has a lateral width of about 50 mm and in some cases may extend along an entire lateral width of the front waist region 22. Suitably, the attachment panel 98 covers about 10% to about 70%, desirably about 20% to about 60% of the surface area of the subassembly 82. Alternatively, the attachment panel 98 may include two similarly-sized attachment panel pieces positioned on the subassembly 82, wherein a fastener 60 is refastenably engageable with a corresponding attachment panel piece. In such an embodiment, each attachment panel piece desirably has a lateral width of about 25 mm to correspond to a width of the corresponding engageable fastener 60.

The multiple component attachment assembly 80 allows the function of the front waist region ears 84 and 86 to be decoupled from the function of the attachment panel engagement with the fasteners 60. This decoupling minimizes the use of relatively higher cost PUB material, for example, while improving the incidence of the proper engagement of the hook-to-loop fastening system of the diaper 20. Further, the multiple component attachment assembly 80 provides an improved fastening system for the diaper 20 without interfering with or limiting the extensibility of the underlying extensible diaper materials and/or components, such as the extensible outer cover 42 to which the attachment assembly 80 is bonded or applied.

The bodyside liner 44 suitably presents a bodyfacing surface that is compliant, soft feeling, and nonirritating to the wearer's skin. In accordance with one embodiment of this invention, the bodyside liner 44 is desirably made of an elastic and/or an extensible material. For example, the bodyside liner 44 may be made from extensible materials as are described in U.S. patent application Ser. No. 09/563,417 filed on May 3, 2000 by Roessler et al. Desirably, these materials are elastic or extensible in at least a lateral direction, parallel to the lateral axis depicted by arrow 40 in FIG. 4.

Further, the bodyside liner 44 may be less hydrophilic than the absorbent core 28 to present a relatively dry surface to the wearer and may be sufficiently porous to be liquid permeable, permitting liquid to readily penetrate through its thickness. Suitable web materials for manufacturing the bodyside liner 44 include, but are not limited to, porous foams, reticulated foams, apertured plastic films, natural fibers (for example, wood or cotton fibers), synthetic fibers (for example, polyester or polypropylene fibers), and/or a combination of natural and synthetic fibers. The bodyside liner 44 is suitably employed to help isolate the wearer's skin from liquids held in the absorbent core 28.

Various woven and nonwoven fabrics can be used for the bodyside liner 44. For example, the bodyside liner 44 may be composed of a meltblown or spunbond web of polyolefin fibers. The bodyside liner 44 may also be a bonded-carded web composed of natural and/or synthetic fibers. The bodyside liner 44 may be composed of a substantially hydrophobic material, and the hydrophobic material may optionally be treated with a surfactant or otherwise processed to impart a desired level of wettability and hydrophilicity. In one embodiment of the invention, the bodyside liner 44 is made from a nonwoven, spunbond, polypropylene fabric composed of about 2.8 to about 3.2 denier fibers formed into a web having a basis weight of about 20 grams per square meter and a density of about 0.13 grams per cubic centimeter. The fabric may be surface treated with about 0.3 weight percent of a surfactant commercially available from Hodgson Textile Chemicals, Inc. under the trade designation AHCOVEL Base N-62. The surfactant may be applied by any conventional means, such as spraying, printing, brush coating or the like. The surfactant may be applied to the entire bodyside liner 44 or may be selectively applied to particular sections of the bodyside liner 44, such as the medial section along the longitudinal centerline of the diaper, to provide greater wettability of such sections. The bodyside liner 44 may further include a lotion or treatment applied thereto that is configured to be transferred to the wearer's skin.

The absorbent core 28 of the diaper 20 may suitably be composed of a matrix of hydrophilic fibers, such as a web of cellulosic fluff, mixed with particles of a high-absorbency material commonly known as superabsorbent material. In one embodiment of this invention, the absorbent core 28 includes a matrix of cellulosic fluff such as wood pulp fluff and superabsorbent hydrogel-forming particles. The wood pulp fluff may be exchanged with synthetic, polymeric, meltblown fibers, or with a combination of meltblown fibers and natural fibers. The superabsorbent particles may be substantially homogeneously mixed with the hydrophilic fibers or may be nonuniformly mixed. The fluff and superabsorbent particles may also be selectively placed into desired zones of the absorbent core 28 to better contain and absorb body exudates. The concentration of the superabsorbent particles may also vary through the thickness of the absorbent core 28. Alternatively, the absorbent core 28 may comprise a laminate of fibrous webs and superabsorbent material or other suitable means of maintaining a superabsorbent material in a localized area.

The absorbent core 28 may have any suitable shape. For example, the absorbent core 28 may be rectangular, I-shaped, or T-shaped. Desirably, the absorbent core 28 is narrow in the crotch region 26 of the diaper 20. The width of the absorbent core 28 in the crotch region 26 desirably is about 2.5 centimeters to about 12.7 centimeters (1.0 inch to about 5.0 inches), more desirably not greater than about 7.6 centimeters (3.0 inches) and even more desirably not greater than about 5.1 centimeters (2.0 inches). The narrow width of the absorbent core 28 in the crotch region 26 allows the absorbent core 28 to better fit between the legs of the wearer. It is apparent that the dimensions and the absorbent capacity of the absorbent core 28 should properly correspond to the size of the intended wearer and the liquid loading imparted by the intended use of the diaper 20.

Suitable high-absorbency materials for the absorbent core 28 include, but are not limited to, natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of suitable synthetic, polymeric, high-absorbency materials include, but are not limited to, the alkali metal and ammonium salts of poly(acrylic acid) and poly (methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core 28 include, but are not limited to, natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and similar compounds. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. Generally, it is desired that the high absorbency material be in the form of discrete particles. However, the high absorbency material may also be in the form of fibers, flakes, rods, spheres, needles, or the like. Generally, the high absorbency material is present in the absorbent core 28 in an amount of about 5 weight percent to about 90 weight percent, based on a total weight of the absorbent core 28.

In accordance with one embodiment of this invention, a substantially hydrophilic tissue wrapsheet (not shown) may be employed to help maintain the integrity of the airlaid fibrous structure of the absorbent core 28. The tissue wrapsheet is typically placed about the absorbent core 28 over at least one of the major facing surfaces thereof and composed of an absorbent cellulosic material, such as creped wadding or a high wet-strength tissue. In accordance with one embodiment of the invention, the tissue wrapsheet can be configured to provide a wicking layer that helps to rapidly distribute liquid over the mass of absorbent fibers comprising the absorbent core 28. The tissue wrapsheet on one side of the absorbent fibrous mass may be bonded to the tissue wrapsheet located on the opposite side of the fibrous mass to effectively entrap the absorbent core 28. In accordance with one embodiment of this invention, the tissue wrapsheet may be necked, pleated and/or have any suitable design known to those having ordinary skill in the art to extend in at least one direction, for example the lateral or cross-machine direction, without tearing or ripping.

In accordance with one embodiment of this invention as shown in FIG. 4, the diaper 20 includes a pair of containment flaps 56 that are configured to provide a barrier to the lateral flow of body exudates. The containment flaps 56 may be located along the laterally opposing side edges 30 of the diaper 20 adjacent the side edges of the absorbent core 28. Each containment flap 56 typically defines an unattached edge that is configured to maintain an upright, perpendicular configuration in at least the crotch region 26 of the diaper 20 to form a seal against the wearer's body. Each containment flap 56 extends longitudinally along at least a portion of a length of the absorbent core 28. Desirably, each containment flap 56 extends along substantially the entire length of the absorbent core 28 to better contain the body exudates. In accordance with one embodiment of this invention wherein each containment flap 56 extends along a portion of the length of the absorbent core 28, the containment flaps 56 can be selectively positioned along the side edges 30 of the diaper 20 in the crotch region 26. Such containment flaps 56 are generally well known to those skilled in the art. For example, suitable constructions and arrangements for containment flaps 56 are described in U.S. Pat. No. 4,704,116, issued Nov. 3, 1987 to K. Enloe, the disclosure of which is hereby incorporated by reference.

In accordance with one embodiment of this invention, at least a portion of the waist edges 32 and the side edges 30 are elastic or extensible to improve the fit range of the diaper 20 and support the absorbent core 28 to prevent leakage of body exudates. For example, referring to FIGS. 1–4, the diaper 20 may include a pair of leg elastic members 54 that are connected to the laterally opposing side edges 30 of the diaper 20 in the crotch region 26. The leg elastic members 54 are generally adapted to fit about the legs to maintain a positive, contacting relationship with the wearer to effectively reduce or eliminate the leakage of body exudates from the diaper 20.

Materials suitable for use as the leg elastic members 54 are well known to those skilled in the art. For example, sheets, filaments, strands or ribbons of a polymeric, elastomeric material may be adhered to the outer cover 42 in a stretched position or attached to the outer cover 42 while the outer cover 42 is pleated, such that elastic constrictive forces are imparted to the outer cover 42. The leg elastic members 54 may also include such materials as polyurethane, synthetic rubber and natural rubber.

In accordance with one embodiment of this invention as shown in FIG. 4, the diaper 20 includes a fit panel 48 superimposed adjacent to the waist edge 32 in at least one of the front waist region 22 and the back waist region 24 to provide a more comfortable, contouring fit about the wearer. Desirably, the fit panel 48 is elastic, elastomeric or extensible in at least one direction, such as the cross-machine or lateral direction. For example, as shown in FIG. 4, the diaper 20 includes an elastomeric fit panel 48 on the interior surface 34 of the diaper 20 that is configured to elongate in the lateral direction to provide an improved fit range and enhanced appearance of the diaper 20. Desirably, the elastic or extensible fit panel 48 allows the waist opening 33 to be adjusted to assist in applying the diaper 20 onto the wearer. The fit panel 48 is also configured with respect to the diaper 20 such that the absorbent core 28 has the ability to move and receive body exudates without adversely affecting the positioning of the fit panel 48 and the diaper 20 about the waist of the wearer. Thus, movements of the wearer may cause the absorbent core 28 to move but do not adversely affect the overall positioning and fit of the diaper 20 on the wearer. Such improved fit can result in reduced leakage from the diaper 20, increased comfort, and a more aesthetically pleasing appearance.

As shown in FIG. 4, in accordance with one embodiment of this invention, the fit panel 48 is located on the interior surface 34 and extends longitudinally beyond the side edges of the absorbent core 28 so that the fit panel 48 is generally coterminous with the waist edge 32 in the respective front waist region 22 and/or back waist region 24.

Suitable materials for producing the fit panel 48 include, but are not limited to, stretch-bonded laminate (SBL) materials, neck-bonded laminate (NBL) materials, elastomeric films, elastomeric foam materials, and/or the like. For example, suitable meltblown elastomeric fibrous webs are described in U.S. Pat. No. 4,663,220, issued May 5, 1987 to T. Wisneski et al., the disclosure of which has previously been incorporated herein by reference. Examples of suitable composite fabrics comprising at least one layer of a nonwoven material secured to a fibrous elastic layer are described in European Patent Application No. EP 0 217 032 published on Apr. 8, 1987 with the inventors listed as J. Taylor et al., the disclosure of which has previously been incorporated herein by reference.

In accordance with one embodiment of this invention, the fit panel 48 may be attached to the diaper 20 in any suitable manner that provides the desired elastic or extensible properties. For example, the fit panel 48 may be attached to the diaper 20 using adhesive, ultrasonic, and/or thermal bonding techniques, and the like.

Referring to FIGS. 1–5, in accordance with one embodiment of this invention, the diaper 20 includes a fastening system 59 having at least one, and desirably two laterally opposing refastenable fasteners 60. The fasteners 60 are permanently bonded, adhered or otherwise attached directly or indirectly to the outer cover 42 of the diaper 20 at or laterally inward from its side edges 30, in one of the front waist region 22 and the back waist region 24. The fasteners 60 may be permanently bonded or attached in the vicinity of the side edges 30 of the diaper 20 by any means known to those skilled in the art, such as adhesive bonds, sonic bonds and/or thermal bonds. Desirably, the fasteners 60 are permanently bonded or attached to the back waist region 24, as shown in FIG. 4. Alternatively, the fasteners 60 may be permanently bonded or attached directly to the extensible fit panel 48 attached to the back waist region 24.

In accordance with one embodiment of this invention as shown in FIG. 3, each fastener 60 may include an extensible portion 62 and a waist size adjustment means, for example a fastening portion 64. The extensible portion 62 may be permanently bonded or attached to the side edge 30 in one of the front waist region 22 and/or the back waist region 24. Desirably, the extensible portion 62 is bonded to the side edge 30 of the back waist region 24. Suitable materials for the extensible portion 62 include, but are not limited to, stretch-bonded laminate (SBL) materials, neck-bonded laminate (NBL) materials, elastomeric films, elastomeric foam materials, laminates of nonwoven webs with elastomeric strands, filaments or films, and the like, such as described above as being suitable for the fit panel 48. Desirably, the extensible portion 62 comprises a neck-bonded laminate material or a stretch-bonded laminate material.

At least a portion of each fastener 60, for example the fastening portion 64, can be releasably engagable with the attachment panel 98 positioned on the subassembly 82 applied to the outer cover 42. The fastening portions 64 of the fasteners 60 are configured to encircle the hips of the wearer and engage the attachment panel 98 to reduce the waist perimeter dimension of the waist opening 33 and conform the waist opening 33 to the wearer's waist. The waist perimeter dimension is a peripheral or circumferential measurement of the waist opening 33, which should generally correspond to the waist of the wearer during use of the diaper 20. It is apparent that the fastening portion 64 may alternatively be located on the front waist region 22 and may be configured to releasably engage a attachment panel 98 positioned on a subassembly 82 applied to the back waist region 24. Alternatively, the diaper 20 may include a fastening portion 64 extending from a single fastener 60.

As shown in FIG. 3, the fasteners 60 may include an intermediate portion 76 between the extensible portion 62 and the fastening portion 64. For example, when the fastener 60 includes hook-type fastener elements on the fastening portion 64, the intermediate portion 76 may be devoid of hook-type fastener elements. Desirably, the intermediate portion 76 is made of an inelastic or non-extensible material.

In accordance with one embodiment of this invention, the intermediate portion 76 of the fastener 60 may include a hinge to which the extensible portion 62 and the fastening portion 64 are attached. When the intermediate portion 76 is configured as a hinge, the fastener 60 desirably is thinner at the intermediate portion 76, and therefore more flexible for easier attachment of the fastening portion 64 to the attachment panel 98.

Desirably, the fastening portion 64 is made of a suitable releasably engageable fastener, such as an adhesive tape tab fastener, hook fastener, loop fastener, mushroom fastener, snap, pin, belt and the like, and combinations thereof. For example, as shown in FIG. 3, the fastening portion 64 may include a plurality of hook-type fasteners and the attachment panel 98 may be configured to function as a complimentary loop-type fastener.

After the initial donning of the diaper 20, at least one of the refastenable fasteners 60 provides the waist size adjustment means for adjusting the waist perimeter dimension of the waist opening 33, as shown in FIG. 1. With the diaper 20 positioned about the waist of the wearer, the waist perimeter dimension may be adjusted by unfastening at least one of the fasteners 60 from the attachment panel 98 and refastening the at least one fastener 60 at a lateral position along the attachment panel 98 to either reduce or increase the waist perimeter dimension corresponding to the waist opening 33. Thus, it is desirable that the waist size adjustment means define a relatively low peel strength such that the caregiver can readily disengage the waist size adjustment means from the diaper 20. Suitable peel strength values are well known to those skilled in the art. One test for measuring peel strength of hook and loop fasteners is ASTM D1876-72. This test is described in U.S. Pat. No. 5,176,671, issued to Roessler et al., the disclosure of which is incorporated herein by reference.

In accordance with one embodiment of this invention, the fasteners 60 are refastenably engaged with the attachment assembly 80 positioned on the outer surface 36 of the front waist region 22 before the diaper 20 is placed on the wearer to provide a disposable refastenable, prefastened diaper 20. In such a configuration, the diaper 20 can be pulled on or off over the legs and hips of the wearer. If the diaper 20 becomes soiled during use, the fasteners 60 can be disengaged to easily remove the diaper 20 from the waist of the wearer with reduced risk of undesirably soiling the clothes or legs of the wearer. Thus, the diaper 20 is configured to be pulled on or off over the hips of the wearer such as conventional training pants and can be readily applied or removed by disengaging the fasteners 60, similar to conventional diaper articles. Moreover, the fasteners 60 can be repositioned after initial donning if necessary to adjust the fit of the diaper 20 to the wearer.

Alternatively, the fasteners 60 can be folded such that the fasteners 60 are releasably engaged with the outer surface 36 of the back waist region 24 before the diaper 20 is placed on the wearer. In such a configuration, the diaper 20 can be pulled on over the legs and hips of the wearer without the fasteners 60 engaging other components of the diaper 20 or any surrounding material that makes it difficult to apply the diaper 20. After the initial donning of the diaper 20, the fasteners 60 can be disengaged from the back waist region 24 and engaged with the attachment panel 98 of the attachment assembly 80 positioned on the front waist region 22 to adjust the waist perimeter dimension to properly fit the waist of the wearer.

EXAMPLE

Figure 7:
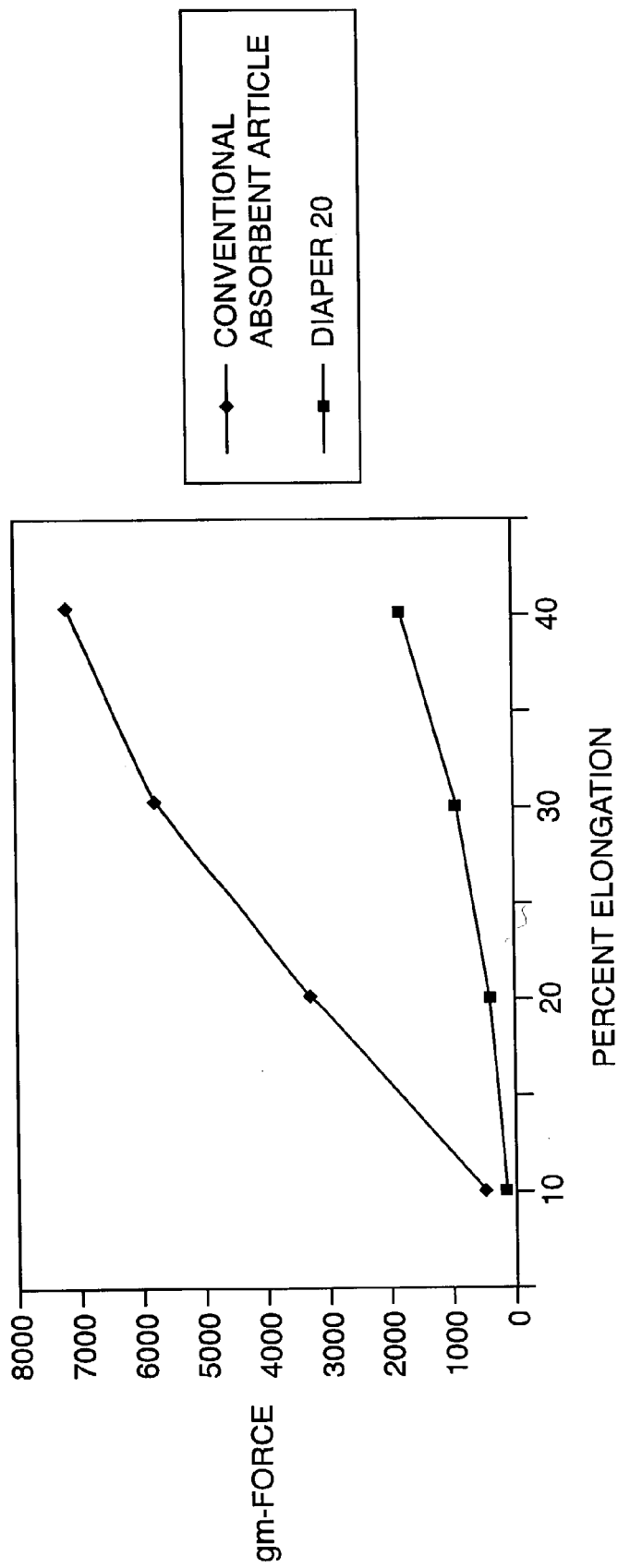
FIG. 7 displays the results of a Front Ear Chassis Tensile Test conducted according to ASTM D2433 test method, to compare the extensibility of a diaper manufactured according to one embodiment of this invention with the extensibility of conventional absorbent articles.

The cross-machine or lateral extensibility of the diaper 20 at the front waist region 22, having an attachment assembly 80 according to one embodiment of this invention, was compared to the cross-machine or lateral extensibility of a conventional absorbent article at a front waist region, having a loop patch comprising a non-extensible PUB material, using a Front Ear Chassis Tensile Test in accordance with ASTM D2433 test method. Three samples of each of the diaper 20 and the conventional absorbent article were tested for lateral extensibility. As shown in FIG. 7, the lower values and flatter line registered by the diaper 20 in accordance with one embodiment of this invention demonstrates that the diaper 20 has a greater cross-machine or lateral elongation potential than does the conventional absorbent article, at any given amount of elongation, at least up to about 40% elongation.

The attachment assembly 80 of this example of the invention includes a subassembly 82, which is adhesively bonded to the exterior surface 36 of the diaper 20. Two pieces of spunbond material were cut to a lateral length, i.e. corresponding to the cross-machine or lateral direction of the diaper 20, and a longitudinal width, i.e. corresponding to the longitudinal direction of the diaper 20. Each spunbond piece was cut so as to have an extensibility in the lateral direction. Two strips of SMS material were cut to having a lateral length of about 30 mm to about 35 mm and a longitudinal width about equal to the longitudinal width of the cut spunbond pieces. The SMS material strips were attached to opposing lateral end portions of one piece of spunbond material, using double-sided adhesive tape. After the SMS strips were securely attached to the spunbond material, the second spunbond material was superposed on the first spunbond material and attached to each SMS material strip and a central region of the first spunbond material, using double-sided tape, to form the subassembly 82.

An attachment panel 98 having a lateral length of about 117 mm and a longitudinal width of about 51 mm, was placed on an outer surface of one spunbond material. The attachment panel 98 was positioned about 15 mm from a lateral edge of the spunbond material. The subassembly 82 was then adhesively bonded to the exterior surface of the diaper 20. In this example, the edge portion of each piece of spunbond material, including the SMS material strip, extends laterally outwardly from the corresponding lateral edge of the diaper chassis. The subassembly 82 has a lateral length about equal to a lateral length of the conventional loop patch, described below in reference to the comparative conventional absorbent article.

The conventional absorbent article compared to the diaper 20 of the present invention included a loop patch comprising a non-extensible PUB material that extends along a lateral length of the front waist region of the absorbent article and laterally outwardly from each of the lateral edges of the absorbent article chassis. The non-extensible PUB material was adhesively bonded to an outer surface of the absorbent article and positioned at a top longitudinal edge of the absorbent article.

Test Method

ASTM D2433 test method, the description of which is incorporated herein by reference, was used to test and compare the cross-machine or lateral extensibility of the diaper 20 having an attachment assembly 80 according to one embodiment of this invention to the cross-machine or lateral extensibility of a conventional absorbent article having a loop patch comprising a non-extensible PUB material. Three samples of each of the diaper 20 and the conventional absorbent article were tested for lateral extensibility.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. An absorbent article comprising:
    a chassis having a front waist region, a back waist region and a crotch region intermediate the front waist region and the back waist region;
    a subassembly including at least a first material layer permanently bonded to the front waist region, the first material layer extending laterally beyond opposing side edges of the front waist region to form a layer of a first front ear and a layer of a laterally opposing second front ear;
    an attachment panel permanently bonded to the subassembly such that the subassembly is between the chassis and the attachment panel; and
    at least one fastener releasably engageable with the attachment panel; and
    wherein the first material layer comprises a first spunbond layer and the subassembly further comprises:
    a first material strip attached to the first material layer and positioned longitudinally at a first end portion of the first material layer;
    a second material strip attached to the first material layer and positioned longitudinally at a second end portion of the first material layer; and
    a second spunbond layer covering at least a portion of the first material strip and at least a portion of the second material strip.

2. The absorbent article of claim 1 wherein the at least one fastener is permanently connected to the back waist region.

3. The absorbent article of claim 1 wherein at least one of the first material strip and the second material strip comprises a SMS laminate material.

4. The absorbent article of claim 1 wherein at least one of the first material strip and the second material strip comprises at least one of a polyethylene material and a polypropylene material.

5. The absorbent article of claim 1 wherein the subassembly comprises a layer of nonwoven spunbond material.

6. The absorbent article of claim 1 wherein the chassis further comprises:
    an extensible outer cover;
    a bodyside liner at least partially bonded to the extensible outer cover; and
    an absorbent core positioned between the extensible outer cover and the bodyside liner.

7. The absorbent article of claim 1 wherein the attachment panel comprises a non-extensible material.

8. An attachment assembly for an absorbent article comprising a chassis having a front waist region, a back waist region and a crotch region intermediate the front waist region and the back waist region, the attachment assembly comprising:
    a subassembly including a first material layer permanently bonded to the front waist region, the first material layer extending laterally beyond a first side edge of the front waist region to form a layer of a first front ear and extending laterally beyond a second side edge of the front waist region to form a laterally opposing second front ear; and
    an attachment panel permanently bonded to the subassembly and releasably engageable with at least one fastener connected with respect to the back waist region, wherein the subassembly is between the chassis and attachment panel; and
    wherein the subassembly further comprises a material strip positioned at an end portion of the first front ear and a material strip positioned at an end portion of the second front ear.

9. The attachment assembly of claim 8 wherein the subassembly comprises a nonwoven web.

10. The attachment assembly of claim 8 wherein the subassembly comprises one of a meltblown web, a spunbond web and a bonded-carded web.

11. The attachment assembly of claim 8 wherein a second layer of material is applied over each material strip.

12. The attachment assembly of claim 8 wherein each material strip comprises a SMS material.

13. The attachment assembly of claim 8 wherein each material strip comprises a polypropylene material.

14. The attachment assembly of claim 8 wherein the attachment panel comprises a pattern unbonded material.

15. The attachment assembly of claim 8 wherein the subassembly comprises a second layer of material positioned on the first layer in a superposed relation.

16. A disposable diaper comprising:
an extensible outer cover;
a bodyside liner;
an absorbent core positioned between the extensible outer cover and the bodyside liner;
a chassis defined by the extensible outer cover, the absorbent core and the bodyside liner, the chassis defining a front waist region, a back waist region and a crotch region intermediate the front waist region and the back waist region; and
a multiple component attachment assembly comprising a subassembly permanently bonded to an exterior surface of the front waist region and forming laterally opposing front ears, and an attachment panel permanently bonded to the subassembly such that the subassembly is between the chassis and the attachment panel;
wherein the subassembly includes at least a first material layer extending laterally beyond a first side edge and a second side edge of the front waist region to form a layer of each laterally opposing front ear; and
wherein the subassembly further comprises a second material layer superposed on the first material layer and a material strip positioned between the first material layer and the second material layer at each of laterally opposing end portions of the subassembly, each material strip extending longitudinally along the corresponding end portion.

17. The disposable diaper of claim 16 wherein the first material layer and the second material layer each comprises one of a spunbond web, a meltblown web and a bonded-carded web.

18. The disposable diaper of claim 16 wherein the material strip comprises a SMS material.

19. The disposable diaper of claim 16 wherein the first material layer comprises a layer of nonwoven spunbond material.

* * * * *